United States Patent
Medoff et al.

(10) Patent No.: US 10,508,293 B2
(45) Date of Patent: *Dec. 17, 2019

(54) PROCESSING BIOMASS

(71) Applicant: XYLECO, INC., Woburn, MA (US)

(72) Inventors: Marshall Medoff, Brookline, MA (US); Thomas Craig Masterman, Rockport, MA (US); Michael W. Finn, Somerville, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/886,478

(22) Filed: Oct. 19, 2015

(65) Prior Publication Data

US 2016/0040204 A1 Feb. 11, 2016

Related U.S. Application Data

(63) Continuation of application No. 14/016,471, filed on Sep. 3, 2013, now abandoned, which is a continuation of application No. PCT/US2012/071093, filed on Dec. 20, 2012.

(60) Provisional application No. 61/579,552, filed on Dec. 22, 2011, provisional application No. 61/579,559, filed on Dec. 22, 2011.

(51) Int. Cl.
| | | |
|---|---|---|
| *C12P 19/24* | (2006.01) | |
| *C12P 19/14* | (2006.01) | |
| *C12P 7/16* | (2006.01) | |
| *C12P 19/02* | (2006.01) | |
| *C12P 7/10* | (2006.01) | |

(52) U.S. Cl.
CPC .............. *C12P 19/24* (2013.01); *C12P 7/10* (2013.01); *C12P 7/16* (2013.01); *C12P 19/02* (2013.01); *C12P 19/14* (2013.01); *C12P 2201/00* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 2,709,699 A * | 5/1955 | Wolf | ............... | C08B 37/0057 536/128 |
| 5,798,237 A | 8/1998 | Picataggio et al. | | |
| 5,951,777 A | 9/1999 | Nurmi et al. | | |
| 7,083,955 B2 | 8/2006 | Otto | | |
| 2002/0132313 A1 | 9/2002 | Lin et al. | | |
| 2008/0138872 A1 * | 6/2008 | Smith | ............... | C12P 7/10 435/165 |
| 2008/0227162 A1 * | 9/2008 | Varanasi | ............... | C12P 7/10 435/96 |
| 2009/0246843 A1 | 10/2009 | Edlauer et al. | | |
| 2010/0112242 A1 | 5/2010 | Medoff | | |
| 2010/0200806 A1 | 8/2010 | Medoff et al. | | |
| 2010/0279371 A1 | 11/2010 | Soong et al. | | |
| 2010/0285552 A1 | 11/2010 | Varanasi et al. | | |
| 2010/0297705 A1 | 11/2010 | Medoff et al. | | |

FOREIGN PATENT DOCUMENTS

| | | |
|---|---|---|
| CN | 101434969 | 5/2009 |
| CN | 101705255 | 5/2010 |
| CN | 102066063 | 5/2011 |
| CN | 102076862 | 5/2011 |
| JP | H10215887 | 8/1998 |
| JP | 2001000200 | 1/2001 |
| JP | 2001518790 | 10/2001 |
| JP | 2009531025 | 9/2009 |
| JP | 2009296919 | 12/2009 |
| JP | 2010508390 | 3/2010 |
| JP | 2011514403 | 5/2011 |
| RU | 2159816 | 11/2000 |
| WO | 199713842 | 4/1997 |
| WO | 2006004748 | 1/2006 |
| WO | 2008073186 | 6/2008 |
| WO | 2009003167 | 12/2008 |
| WO | 2010046532 | 4/2010 |
| WO | 2010093829 | 8/2010 |
| WO | 2011133536 | 10/2011 |
| WO | 2012092431 | 7/2012 |

OTHER PUBLICATIONS

Pena et al., Cellobiose Hydrolysis Using Acid-functionalized Nanoparticles, Biotechnology and Bioprocess Engineering, vol. 16: pp. 1214-1222, 2011.*
Marshall et al., Enzymatic Conversion of D-Glucose to D-Fructose, Science, vol. 125 (3249), pp. 648-649, Apr. 5, 1957.*
Zhou et al., Catalytic conversion of lignocellulosic biomass to fine chemicals and fuels, Chem. Soc. Rev., 2011, 40, 5588-5617.*
Dow Amberlyst™ 15Dry Product Data Sheet, retrieved from the internet: http://msdssearch.dow.com/PublishedLiteratureDOWCOM/dh_08d2/0901b803808d2f04.pdf?filepath=liquidseps/pdfs/noreg/177-03086.pdf&fromPage=GetDoc.*
Sigma Product Information Brochure, Cellobiase from Aspergillus Niger, Retrieved from the Internet May 28, 2015: http://www.sigmaaldrich.com/catalog/product/sigma/c6105?lang=en&region=US#.
Zhou et al., "Catalytic Conversion of Lignocellulosic Biomass to Fine Chemicals and Fuels", Chem. Soc. Rev., vol. 40, 2011, pp. 5588-5617, published Aug. 24, 2011.

(Continued)

*Primary Examiner* — Thomas J. Visone
*Assistant Examiner* — Evelyn Y Pyla
(74) *Attorney, Agent, or Firm* — Leber IP Law; Shelly Fujikawa

(57) ABSTRACT

Provided herein are methods of increasing the efficiency of biomass saccharification. In particular, the methods include ways of avoiding feedback inhibition of enzymatic reactions during the production of useful products. The methods also include saccharifying recalcitrance-reduced lignocellulosic biomass and adding an isomerization agent to the saccharified biomass. The saccharified biomass can be further converted into products by a microorganism.

16 Claims, 2 Drawing Sheets

(56) References Cited

OTHER PUBLICATIONS

Nakata et al., "Ethanol Production With Beta-Xylosidase, Xylose Isomerase, and *Saccharomyces cerevisiae* From the Hydrolysate of Japanese Beech After Hot-Compressed Water Treatment", Journal of Wood Science, vol. 55, 2009, pp. 289-294.
Hughes et al., "Automated Yeast Transformation Protocol to Engineer *Saccharomyces cerevisiae* Strains for Cellulosic Ethanol Production with Open Reading Frames That Express Proteins Binding to Xylose Isomerase Identified Using a Robotic Two-Hybrid Screen", Journal of Laboratory Automation, vol. 14, 2009, pp. 200-212.
Yuan et al., "Fermentation of Biomass Sugars to Ethanol Using Native Industrial Yeast Strains", Bioresource Technology, vol. 102, Nov. 13, 2010, pp. 3246-3253.
Silva et al., "An Innovative Biocatalyst for Production of Ethanol From Xylose in a Continuous Bioreactor", Enzyme and Microbial Technology, vol. 50, Jan. 5, 2012, pp. 35-42.
Office Action—Corresponding EP Application No. 12821219.8, dated Nov. 9, 2015, 6 pages.
P. Chandrakant et al., "Simultaneous Bioconversion of Glucose and Xylose to Ethanol to *Saccharomyces cerevisiae* in the Presence of Xylose Isomerase", Appl. Microbiol. Biotechnol. (2000) 53: 301-309.
Lew et al., One-Pot Synthesis of 5-(Ethoxymethyl)furfural from Glucose Using Sn-BEA and Abmerlyst Catalysts, Industrial and Engineering Chemistry Research, 2012, vol. 51, pp. 5364-5366.
Bhosale et al., Molecular and Industrial Aspects of Glucose Isomerase, Microbioilogical Reviews, Jun. 1996, vol. 60, No. 2, pp. 280-300.
Deng et al., "Acid-Catalysed Direct Transformation of Cellulose into Methyl Glucosides in Methanol at Moderate Temperatures", Chem. Commun., 2010, vol. 46, pp. 2668-2670.
Suganuma et al., Hydrolysis of Cellulose by Amorphous Carbon Bearing SO3H, COOH, and OH Groups, JACS, published on Web Aug. 29, 2008, vol. 130, pp. 12787-12793.
Chen Hongzhang, Process Engineering in Plant-Based Products:, http://img.duxiu.com/n/print.jsp, Sep. 23, 2016, 4 pages.
Search Report—Corresponding Chinese application No. 2012800628537, dated Sep. 26, 2016, 2 pages.
Onda A. et al., "Selective Hydrolysis of Cellulose into Glucose over Solid Acid Catalysts", Green Chemistry, 2008, 10, pp. 1033-1037.
Arai M. et al., "Conversion of Rice Straw to Ethanol by Simultaneous Saccharification and Fermentation", Department of Agricultural Chemistry, College of Agriculture, University of Osaka Prefecture, Sakai, Osaka 591, Japan, Hakkokogaku, 63:427-431, 1985.
Lin, S.J. et al., "High-Level Production of Erythritol by Mutants of *Osmophilic moniliella* sp.", Process Biochemistry, vol. 45, 2010, pp. 973-979.
Guio F. et al., "Kinetic Modeling of the Fructooligosaccharides Production by Aspergillus Oryzae N74 and immobilized Glucose Isomerase at Bench Scale", Abstracts/Current Opinion in Biotechnology, vol. 225, 2011, p. 534.
Office Action—Corresponding Japanese Application No. 2014-548923, dated Sep. 20, 2016, 6 pages.

Search Report dated Aug. 7, 2017, issued by the Eurasian Patent Office in related Eurasian Patent Application No. 201790303 (4 pages).
Smuk, J.M. et al., "Rate of D-Xylose Decomposition in Sulfuric Acid—Sodium 2, 4 Dimethylbenzenesulfonate—Water Solutions", U.S. Department of Agriculture, Forest Service, Forest Products Laboratory, U.S. Forest Service Research Paper FPL, Jan. 20 1965, 15 pages.
Yang, Yu; et al., "Synthesis of Furfural from Xylose, Xylan, and Biomass Using AlCl3 • 6 H2O in Biphasic Media via Xylose Isomerization to Xylulose," ChemSusChem, Feb. 7, 2012, pp. 405-410.
Choudhary, Vinit; et al., "Xylose Isomerization to Xylulose and its Dehydration to Furfural in Aqueous Media," ACS Catalysis, Nov. 9, 2011, 5 pages.
Lima; et al., "Fructose syrup: A biotechnology asset," Food Technology and Biotechnology, Zagreb, Croatia, vol. 49, Accepted Apr. 19, 2010, pp. 424 -434.
Shi; et al., "Large number of phosphotransferase genes in the Clostridium beijerinckii NCIMB 8052 genome and the study on their evolution," BMC Bioinformatics, vol. 11 (Suppl 11), Dec. 14, 2010, pp. 1-8.
Wang; et al., "Optimization of butanol production from tropical maize stalk juice by fermentation with Clostridium beijerinckii NCIMB 8052," Bioresource Technology, vol. 102, Nov. 2011, pp. 9985-9990.
Huang; et al., "Acetic acid production from fructose by Clostridium formicoaceticum immobilized in a fibrous-bed bioreactor," Biotechnology Process, vol. 14, Aug. 27, 1998, pp. 800-806.
Rodríguez; et al., "Mannitol production by heterofermentative Lactobacillus reuteri CRL 1101 and Lactobacillus rermentum CRL 573 in free and controlled pH batch fermentations", Applied Microbiology and Biotechnology, vol. 93, Published online Oct. 13, 2011, pp. 2519-2527.
Yu; et al., "Selective utilization of fructose to glucose by Candida magnoliae, an erythritol producer," Applied Biochemistry and Biotechnology, vol. 129-132, Mar. 2006, pp. 870-879.
Al-Shorgani; et al., "The effect of different carbon sources on biobutanol production using Clostridium saccharoperbutylacetonicum N1-4," Biotechnology, vol. 10, Issue 3, 2011, pp. 280-285.
Ferchichi; et al., "Influence of culture parameters on biological hydrogen production by Clostridium saccharoperbutylacetonicum ATCC 27021," World Journal of Microbiology & Biotechnology, vol. 21, Oct. 2005, pp. 855-862.
English Abstract of Deng; et al. "Acetone-butanol fermentation from the mixture of fructose and glucose," Chinese Journal of Biotechnology, vol. 27, Oct. 2011, 5 pages.
Takagaki; et al., "Glucose production from saccharides using layered transition metal oxide and exfoliated nanosheets as a water-tolerant solid acid catalyst," Chemical Communications, Sep. 16, 2008, pp. 5363-5365.
Search Report issued on Brazilian Application No. BR112014015289-6 dated Aug. 13, 2019, 5 pages.
Notice of Allowance and English Translation, issued on Korean Application No. 10-2014-7017757, dated Sep. 25, 2019, 3 pages.

* cited by examiner

PROCESSING BIOMASS

CROSS REFERENCE TO RELATED APPLICATIONS

This application is a continuation of U.S. patent application Ser. No. 14/016,471, filed Sep. 3, 2013, which is a continuation of PCT/US2012/071093, filed Dec. 20, 2012, which claimed priority from U.S. Provisional Application Nos. 61/579,552 and 61/579,559 both filed on Dec. 22, 2011. The entire disclosures of the above applications are incorporated herein by reference.

FIELD OF THE INVENTION

The invention pertains to efficiencies useful in the processing of biomass materials. For example, the invention relates to processes that circumvent negative feedback of enzymatic reactions.

BACKGROUND

As demand for petroleum increases, so too does interest in renewable feedstocks for manufacturing biofuels and biochemicals. The use of lignocellulosic biomass as a feedstock for such manufacturing processes has been studied since the 1970s. Lignocellulosic biomass is attractive because it is abundant, renewable, domestically produced, and does not compete with food industry uses.

Many potential lignocellulosic feedstocks are available today, including agricultural residues, woody biomass, municipal waste, oilseeds/cakes and sea weeds, to name a few. At present these materials are either used as animal feed, biocompost materials, are burned in a cogeneration facility or are landfilled.

Lignocellulosic biomass is recalcitrant to degradation as the plant cell walls have a structure that is rigid and compact. The structure comprises crystalline cellulose fibrils embedded in a hemicellulose matrix, surrounded by lignin. This compact matrix is difficult to access by enzymes and other chemical, biochemical and biological processes. Cellulosic biomass materials (e.g., biomass material from which substantially all the lignin has been removed) can be more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

While a number of methods have been tried to extract structural carbohydrates from lignocellulosic biomass, they are either too expensive, produce too low a yield, leave undesirable chemicals in the resulting product, or simply degrade the sugars.

Monosaccharides from renewable biomass sources could become the basis of chemical and fuels industries by replacing, supplementing or substituting petroleum and other fossil feedstocks. However, techniques need to be developed that will make these monosaccharides available in large quantities and at acceptable purities and prices.

SUMMARY OF THE INVENTION

Provided herein are methods of increasing the efficiency of saccharification of biomass. In particular, efficiencies can be achieved by avoiding negative feedback inhibition of enzymatic reactions.

Provided herein is a method of making a product, where the method includes: saccharifying recalcitrance-reduced lignocellulosic biomass, and adding an isomerization agent to the saccharified biomass. In some implementations, the saccharified biomass comprises a first sugar and a second sugar and the isomerization agent is used to convert the second sugar to a third sugar. The method may also include, in some cases, contacting the saccharified biomass with a microorganism to convert the first sugar and third sugar to one or more product(s).

Also provided herein is a method of making a product with a microorganism from a first sugar and a second sugar, where the microorganism can convert the first sugar to the product, but cannot metabolize the second sugar, and where the method includes: providing a cellulosic or lignocellulosic biomass; saccharifying the biomass to make a saccharified biomass, wherein the saccharified biomass comprises a first sugar and a second sugar; providing a microorganism that is capable of converting the first sugar into a product, but wherein the microorganism cannot metabolize the second sugar; combining the microorganism and the saccharified biomass, thereby producing a microorganism-biomass combination; maintaining the microorganism-biomass combination under conditions that enable the microorganism to convert the first sugar to the product, producing a combination that comprises the product and the second sugar; converting the second sugar to a third sugar, wherein the microorganism is capable of converting the third sugar to the product; and maintaining the microorganism under conditions that enable the microorganism to convert the third sugar to the product; thereby making a product with a microorganism from the first sugar and the second sugar.

In another aspect, the invention features a method of increasing the amount of a product made by a microorganism from a saccharified biomass, the method comprising: providing a cellulosic or lignocellulosic biomass; saccharifying the biomass to make a saccharified biomass, wherein the saccharified biomass comprises a first sugar and a second sugar; providing a microorganism that is capable of converting the first sugar into a product, but wherein the microorganism cannot metabolize the second sugar; combining the microorganism and the saccharified biomass, thereby producing a microorganism-biomass combination; maintaining the microorganism-biomass combination under conditions that enable the microorganism to convert the first sugar to the product, producing a combination that comprises the product and the second sugar; converting the second sugar to a third sugar, wherein the microorganism is capable of converting the third sugar to the product; and maintaining the microorganism under conditions that enable the microorganism to convert the third sugar to the product; thereby increasing the amount of the product made by the microorganism from the saccharified biomass.

In any of the methods provided herein, the lignocellulosic biomass can be treated to reduce its recalcitrance to saccharification. The treatment method is selected from the group consisting of: bombardment with electrons, sonication, oxidation, pyrolysis, steam explosion, chemical treatment, mechanical treatment, or freeze grinding. The treatment method can be bombardment with electrons.

In any of the methods, the conversion of the second sugar to the third sugar can be done before maintaining the microorganism-biomass combination under conditions that enable the microorganism to convert the first sugar to the product. The conversion of the second sugar to the third sugar can be done immediately after saccharification of the biomass, or it can be done during saccharification of the biomass.

In the methods provided herein, the lignocellulosic biomass can be selected from the group consisting of: wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, agricultural or industrial waste, arracacha, buckwheat, banana, barley, cassava, kudzu, oca, sago, sorghum, potato, sweet potato, taro, yams, beans, favas, lentils, peas, or mixtures of any of these. The lignocellulosic biomass can be mechanically treated to reduce its bulk density and/or increase its surface area. For instance, it can be comminuted, e.g., by dry milling, or by wet milling. The biomass can be saccharified with one or more cellulases.

In the methods provided herein, the isomerization agent can comprise an acid, e.g., polystyrene sulfonic acid.

In the methods provided herein, the microorganism-biomass combination can be maintained at a pH of about 10 to about 14, or at a pH of about 11 to about 13. It can be maintained at a temperature of about 10° C. to about 30° C., or at a temperature of about 20° C. It can also be maintained at a temperature of about 60° C. to about 65° C. It can be maintained at a pH of about 6.0 to about 7.5, or a pH of about 7.

In the methods, the second sugar can be glucose, and the third sugar can be fructose. The isomerization agent can comprise an enzyme. Alternatively, the second sugar can be xylose, and the third sugar can be xylulose. The enzyme can be xylose isomerase.

The microorganism can be yeast. The product can be alcohol. The microorganism can be *Clostridium* spp., and the product can be ethanol, butanol, butyric acid, acetic acid, or acetone. The microorganism can be *Lactobacillus* spp., and the product can be lactic acid.

It should be understood that this invention is not limited to the embodiments disclosed in this Summary, and it is intended to cover modifications that are within the spirit and scope of the invention, as defined by the claims.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

Provided herein are methods of increasing the efficiency of production of sugars (and/or products made from the sugars) from saccharified biomass. The methods are especially useful in cases where one or more sugars or products cause negative feedback, limiting the amount of sugars or products that can be produced.

Typically, the methods begin with saccharifying a biomass. Saccharification usually produces a mixture of sugars. The mixture includes sugars that can be converted to a useful product. However, the mixture of sugars can include sugars that cannot be metabolized by the microorganism. As these non-utilizable sugars increase in concentration, they represent a metabolic "dead-end." Furthermore, some sugars may form the basis of feedback inhibition, and limit the throughput of metabolic pathways that make desired sugars or other desired products.

Disclosed herein are methods for preventing such feedback inhibition, and increasing the amount of sugars and other useful products from the saccharification of biomass.

The glucose produced during saccharification can inhibit further production of glucose. In one embodiment, therefore, the invention encompasses the effective removal of glucose by converting it to fructose (which does not inhibit saccharification), thereby allowing for the production of additional glucose. Glucose can be converted to fructose by the action of enzymes (such as xylose isomerase), strong acids or chemicals (such as polystyrene sulfonic acid). Likewise, xylose, which cannot be metabolized by many microorganisms, can be converted by xylose isomerase into xylulose, which can be metabolized by many microorganisms. In addition, xylulose often does not inhibit its own production, unlike glucose.

For instance, biomass can be saccharified to produce a mixture of sugars, including glucose and xylose. Most yeast strains can metabolize glucose, e.g., to an alcohol, but not xylose. Therefore, if the desired end product is alcohol, then increased saccharification, and increased production of glucose, followed by fermentation, will produce more alcohol, but it will also produce more xylose. While the xylose is not harmful, it can represent a metabolic "dead end." If the xylose is converted to xylulose, it can be fermented to alcohol, and production efficiency can be increased.

Figure 1:
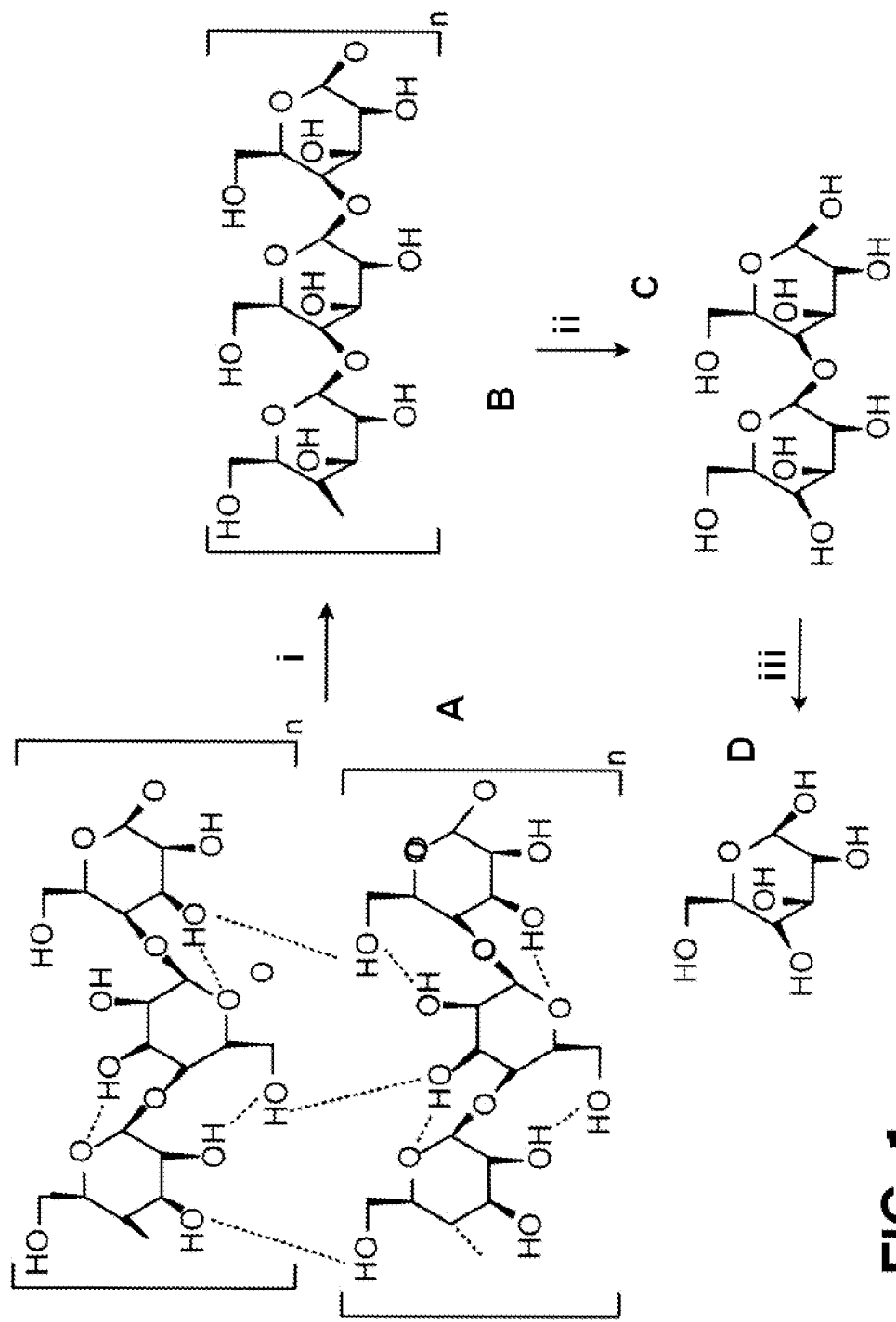
FIG. 1 is a diagram illustrating the enzymatic hydrolysis of cellulose to glucose. Cellulosic substrate (A) is converted by endocellulase (i) to cellulose (B), which is converted by exocellulase (ii) to cellobiose (C), which is converted to glucose (D) by cellobiase (beta-glucosidase) (iii).

As shown in FIG. 1, for example, during saccharification a cellulosic substrate (A) is initially hydrolyzed by endoglucanases (i) at random locations producing oligomeric intermediates (e.g., cellulose) (B). These intermediates are then substrates for exo-splitting glucanases (ii) such as cellobiohydrolase to produce cellobiose from the ends of the cellulose polymer. Cellobiose is a water-soluble 1,4-linked dimer of glucose. Finally, cellobiase (iii) cleaves cellobiose (C) to yield glucose (D). Therefore, the endoglucanases are particularly effective in attacking the crystalline portions of cellulose and increasing the effectiveness of exocellulases to produce cellobiose, which then requires the specificity of the cellobiose to produce glucose. Therefore, it is evident that depending on the nature and structure of the cellulosic substrate, the amount and type of the three different enzymes may need to be modified.

Figure 2:
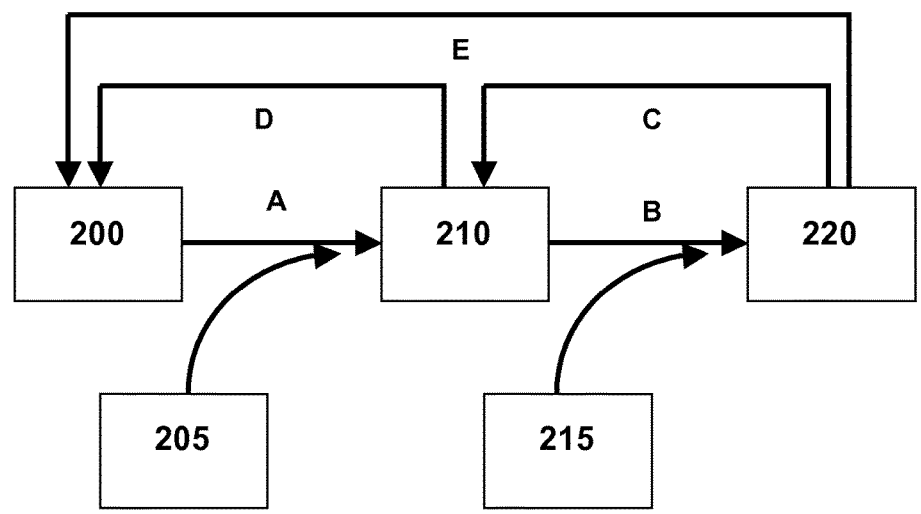
FIG. 2 is a flow diagram illustrating the action of cellulase on cellulose and cellulose derivatives. Cellulose (200) is broken down to cellobiose (210) by endoglucanases and exo-glucanases/cellobiohydrolases (205) (A), which is then broken down by beta-glucosidase (215) to glucose (220) (B). Endoglucanases and exo-glucanases/cellobiohydrolases are directly inhibited by cellobiose (210) (D) and glucose (E), and beta-glucosidase is inhibited by glucose (C).

As shown in FIG. 2, hydrolysis of cellulose (200) to cellobiose (210) is a multi-step process which includes initial breakdown at the solid-liquid interface via the synergistic action of endoglucanases (EG) and exo-glucanases/cellobiohydrolases (CBH) (205) (A). This initial degradation is accompanied by further liquid phase degradation, by hydrolysis of soluble intermediate products such as oligosaccharides and cellobiose that are catalytically cleaved by beta-glucosidase (BG; 215) (B) to glucose (220). However, cellobiose (210) directly inhibits (D) both CBH and EG (205), and glucose (220) directly inhibits (C, E) not only BG (215), but also CBH and EG (205). The invention as described herein reduces or avoids this inhibition.

Figure 3:
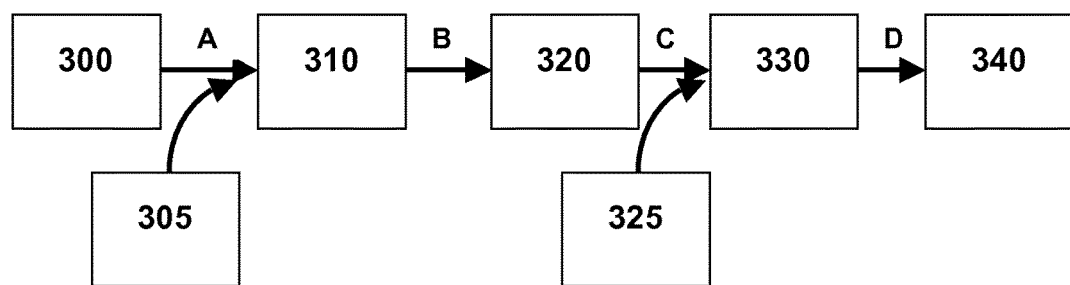
FIG. 3 is a flow diagram illustrating the conversion of biomass (300) to a product (340). The feedstock (300) is combined (A) with cellulase (305) and fluid to form a mixture (310), which is then allowed to saccharify (B), producing sugars (320). As disclosed herein, an additive (325) is combined (C) with the mixture of sugars (320) to make a mixture of sugars and additive (330). The resulting sugars are then used (D) in downstream processing to produce one or more products (340), such as alcohol, lactic acid, or one or more of the sugars themselves.

FIG. 3 shows a process for manufacturing a product (340) from a feedstock (300). The feedstock can be pre-processed, such as by reduction of the size and recalcitrance of the feedstock. This can include, for example, optionally mechanically treating the feedstock and, before and/or after this treatment, optionally treating the feedstock with another treatment, for example, particle bombardment, to further reduce its recalcitrance. The up-stream processed feedstock (300) is then combined (A) with cellulase (305) and fluid to form a mixture (310), which is then allowed to saccharify (B), producing sugars (320). As disclosed herein, an additive (325) is combined (C) with the mixture of sugars (320) to make a mixture of sugars and additive (330). The additive (325) increases the effectiveness of the cellulase during saccharification, e.g., by reducing inhibition of the cellulase by cellobiose and/or glucose. This increased effectiveness of saccharification results in increased levels of sugars, which are then used (D) in downstream processing to produce one or more products (340), such as alcohol, lactic acid, or one or more of the sugars themselves.

During saccharification, the feedstock is treated with one or more cellulolytic enzymes, generally by combining the feedstock and the enzyme (305) in a fluid medium, e.g., an aqueous solution. In some cases, the feedstock is boiled, steeped, or cooked in hot water prior to saccharification, as described in U.S. Pat. App. Pub. 2012/0100577 A1, filed Oct. 18, 2011 and published Apr. 26, 2012, the entire contents of which are incorporated herein by reference.

The additive can be added at the initiation of the saccharification (B), for example, with the biomass and cellulase. Alternatively, the additive can be added after some or all of the saccharification (B) has occurred. It can also be added at the start of producing a product.

The additive can be a chemical or an enzyme. Examples of suitable additives include acids and bases. Bases can catalyze the Lobry-de-Bruyn-Alberda-van-Ekenstein transformation, as described in more detail below. Acids can catalyze the hydrolysis of cellobiose. Boronic acids can be used to complex with the cis-diols of glucose. Xylose isomerase (a.k.a. glucose isomerase) can be used to isomerize glucose to fructose.

The additive can be physically supported. Useful supports include but are not limited to cationic polymeric supports, anionic polymeric supports, neutral polymeric supports, metal oxide supports, metal carbonate supports, metal halide supports and/or mixtures thereof. The support can be added to the mixed sugars or can be stationary and the mixed sugars made to pass through or over the supported additive.

The mixture containing the additive (330) can be returned to the biomass and cellulase stage (310) to release more sugars before being further processed. This can include returning the conditions to a state that preferably causes the saccharification of cellulose rather than conditions that favor the action of the additive. For example, the pH can be optimized for saccharification in the acidic region (less than or equal to pH 7, less than or equal to pH 6, less than or equal to pH 5) and greater than or equal to pH 2 (greater than or equal to pH 3, greater than or equal to pH 4). The temperature can be optimized for the action of cellulases, e.g., to greater than or equal to 30° C. (greater than or equal to 40° C., greater than or equal to 50° C., greater than or equal to 60° C.) and less than or equal to 90° C. (less than or equal to 80° C., less than or equal to 70° C., less than or equal to 60° C.). Additional biomass, cellulase and additive can optionally be added for increased production of sugars.

The sugar solution or suspension produced by saccharification can be subjected to downstream processing to obtain a desired product. For example, one or more of the sugars can be isolated, and/or the solution can be fermented. When fermentation is utilized, the fermentation product can be distilled. For example, sugars can be hydrogenated and sugar alcohols isolated.

Without being bound by any particular theory, it is believed that this conversion effectively removes glucose from the mix of sugars. As shown in FIG. 2, this removal would remove the inhibition steps C and E. This increases the overall saccharification of cellulose in the biomass.

In many instances, the optimum temperature for using glucose isomerase ranges from 60 to 80° C. In the processes described herein, temperatures lower than the optimum may be preferred because of cost and because the optimum temperature for other components of the process can be different. For example cellulase activities are generally optimal between 30° C. and 65° C. A temperature range of about 60° C. to about 65° C. may therefore be preferred, particularly if the glucose isomerase and cellulase are combined and used simultaneously. If they are not used together, then optimal temperatures for each enzyme can be selected.

The optimum pH range for glucose isomerase activity is between pH 7 and 9. As with the selection of the temperature range, in practicing this invention a lower pH can be preferred because in some cases other components of the process may require a lower pH. For example, cellulases are active over a range of pH of about 3 to 7. The preferred pH for the combined enzymes is therefore generally at or below pH 7. If the glucose isomerase and cellulase are not used together, then the optimal pH range for each enzyme can be selected.

Glucose isomerase can be added in any amount. For example, the concentration may be below about 500 U/g of cellulose (lower than or equal to 100 U/g cellulose, lower than or equal to 50 U/g cellulose, lower than or equal to 10 U/g cellulose, lower than or equal to 5 U/g cellulose). The concentration can be at least about 0.1 U/g cellulose to about 500 U/g cellulose, at least about 0.5 U/g cellulose to about 250 U/g cellulose, at least about 1 U/g cellulose to about 100 U/g cellulose, at least about 2 U/g cellulose to about 50 U/g cellulose.

In some cases, the addition of a glucose isomerase increases the amount of sugars produced by at least 5% (e.g., at least 10%, at least 15%, at least 20%, at least 30, 40, 50, 60, 70, 80, 90, 100%).

Another additive that can be used in the invention is, e.g., a chemical that increases the activity of the saccharifying agent. The chemical can be, for example, a chemical that facilitates the Lobry-de-Bruyn-van-Alberda-van-Ekenstein transformation (also called the Lobry-de-Bruyn-van-Ekenstein transformation). This reaction forms an enol from an aldose which can then form a ketose. For example, in the pH range of 11 to 13 and at a temperature of 20° C., alkali will catalyze the transformation of D-glucose into D-fructose and D-mannose. Typically the reaction is base catalyzed, but it can also be acid catalyzed, or take place under neutral conditions. As with the use of glucose isomerase, this reaction effectively removes glucose.

As another example, an acid can be used to catalyze hydrolysis of cellobiose. By using chemical means to cleave cellobiose to glucose, rather than enzymatic or microbial means, inhibition of these reactions by glucose does not occur.

In another example, the chemical can be one that reacts with glucose, such as a boronic acid which binds preferentially to cis-diols.

The chemical can be on a support, for example, by polystyrene sulfonates (such as an Amberlyst™) or polystyrene amines. The mixed sugars can be passed through the supported chemical or flow over it. For example, the chemical can be a polystyrene supported boronic acid. The glucose can be trapped as a borate by the polystyrene support and then released at a later stage, by addition of base for example.

Xylose Isomerase

Xylose isomerase (ES 5.3.1.5) is an enzyme the catalyzes the chemical reaction back and forth between D-xylose and D-xylulose. It is also known systematically as glucose isomerase and D-xylose aldose-ketose isomerase, and belongs to a family of isomerases, specifically those intramolecular oxidoreductases interconverting aldoses and ketoses. Other names in common use include D-xylose isomerase, D-xylose ketoisomerase, and D-xylose ketolisomerase. The enzyme participates in pentose and glucuronate interconversions and fructose and mannose metabolism. It is used industrially to convert glucose to fructose in the manufacture of high-fructose corn syrup. It is sometimes referred to as "glucose isomerase." "Xylose isomerase" and "glucose isomerase" are used interchangeably herein. In vitro, glucose isomerase catalyzes the interconversion of glucose and fructose. In vivo, it catalyzes the interconversion of xylose and xylulose.

Several types of enzymes are considered xylose isomerases. The first kind is produced from *Pseudomonas hydrophile*. This enzyme has 160 times lower affinity to glucose than xylose but nonetheless is useful for increasing the amount of fructose in the presence of glucose. A second kind of enzyme is found in *Escherichia intermedia*. This enzyme is a phophoglucose isomerase (EC 5.3.1.9) and can isomerize unphosphorylated sugar only in the presence of arsenate. A glucose isomerase (EC 5.3.16) can be isolated from *Bacillus megaterium* AI and is NAD linked and is specific to glucose. Another glucose isomerase having similar activity is isolated from *Paracolobacterium aerogenoides*. Glucose isomerases produced by heterolactic acid bacteria require xylose as an inducer and are relatively unstable at high temperature. The xylose isomerase (EC 5.3.1.5) is the most useful for commercial applications as it does not require expensive cofactors such as NAD+ or ATP and it is relatively heat stable.

The glucose isomerases are usually produced intercellularly but reports of extracellular secretion of glucose isomerases are known. The enzyme used can be isolated from many bacteria including but not limited to: *Actinomyces olivocinereus, Actinomyces phaeochromogenes, Actinoplanes missouriensis, Aerobacter aerogenes, Aerobacter cloacae, Aerobacter levanicum, Arthrobacter* spp., *Bacillus stearothermophilus, Bacillus megabacterium, Bacillus coagulans, Bifidobacterium* spp., *Brevibacterium incertum, Brevibacterium pentosoaminoacidicum, Chainia* spp., *Corynebacterium* spp., *Cortobacterium helvolum, Escherichia freundii, Escherichia intermedia, Escherichia coli, Flavobacterium arborescens, Flavobacterium devorans, Lactobacillus brevis, Lactobacillus buchneri, Lactobacillus fermenti, Lactobacillus mannitopoeus, Lactobacillus gayonii, Lactobacillus plantarum, Lactobacillus lycopersici, Lactobacillus pentosus, Leuconostoc mesenteroides, Microbispora rosea, Microellobosporia flavea, Micromonospora coerula, Mycobacterium* spp., *Nocardia asteroides, Nocardia corallia, Nocardia dassonvillei, Paracolobacterium aerogenoides, Pseudonocardia* spp., *Pseudomonas hydrophile, Sarcina* spp., *Staphylococcus bibila, Staphylococcus flavovirens, Staphylococcus echinatus, Streptococcus achromogenes, Streptococcus phaeochromogenes, Streptococcus fracliae, Streptococcus roseochromogenes, Streptococcus olivaceus, Streptococcus californicos, Streptococcus venuceus, Streptococcus virginial, Streptomyces olivochromogenes, Streptococcus venezaelie, Streptococcus wedmorensis, Streptococcus griseolus, Streptococcus glaucescens, Streptococcus bikiniensis, Streptococcus rubiginosus, Streptococcus achinatus, Streptococcus cinnamonensis, Streptococcus fradiae, Streptococcus albus, Streptococcus griseus, Streptococcus hivens, Streptococcus matensis, Streptococcus murinus, Streptococcus nivens, Streptococcus platensis, Streptosporangium album, Streptosporangium oulgare, Thermopolyspora* spp., *Thermus* spp., *Xanthomonas* spp. and *Zymononas mobilis*.

Glucose isomerase can be used free in solution or immobilized on a support. Whole cells or cell free enzymes can be immobilized. The support structure can be any insoluble material. Support structures can be cationic, anionic or neutral materials, for example diethylaminoethyl cellulose, metal oxides, metal chlorides, metal carbonates and polystyrenes. Immobilization can be accomplished by any suitable means. For example immobilization can be accomplished by contacting the support and the whole cell or enzyme in a solvent such as water and then removing the solvent. The solvent can be removed by any suitable means, for example filtration or evaporation or spray drying. As another example, spray drying the whole cells or enzyme with a support can be effective.

Glucose isomerase can also be present in a living cell that produces the enzyme during the process. For example, a glucose isomerase producing bacteria can be co-cultured in the process with an ethanol fermenting bacteria. Alternatively, the glucose-isomerase-producing bacteria can be first contacted with the substrate, followed by inoculating with an ethanol-producing substrate.

Glucose isomerase can also be present within or secreted from a cell also capable of a further useful transformation of sugars. For example, a glucose fermenting species can be genetically modified to contain and express the gene for production of glucose isomerase.

I. Treatment of Biomass Material

A. Particle Bombardment

One or more treatments with energetic particle bombardment can be used to process raw feedstock from a wide variety of different sources to extract useful substances from the feedstock, and to provide partially degraded organic material which functions as input to further processing steps and/or sequences. Particle bombardment can reduce the molecular weight and/or crystallinity of feedstock. In some embodiments, energy deposited in a material that releases an electron from its atomic orbital can be used to treat the materials. The bombardment may be provided by heavy charged particles (such as alpha particles or protons), electrons (produced, for example, in beta decay or electron beam accelerators), or electromagnetic radiation (for example, gamma rays, x rays, or ultraviolet rays). Alternatively, radiation produced by radioactive substances can be used to treat the feedstock. Any combination, in any order, or concurrently of these treatments may be utilized. In another approach, electromagnetic radiation (e.g., produced using electron beam emitters) can be used to treat the feedstock.

Each form of energy ionizes the biomass via particular interactions. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units. Accelerators used to accelerate the particles can be electrostatic DC, electrodynamic DC, RF linear, magnetic induction linear or continuous wave. For example, cyclotron type accelerators are available from IBA (Ion Beam Accelerators, Louvain-la-Neuve, Belgium), such as the Rhodotron™ system, while DC type accelerators are available from RDI, now IBA Industrial, such as the Dynamitron™. Ions and ion accelerators are discussed in Introductory Nuclear Physics, Kenneth S. Krane, John Wiley & Sons, Inc. (1988), Krsto Prelec, FIZIKA B 6 (1997) 4, 177-206; Chu, William T., "Overview of Light-Ion Beam Therapy", Columbus-Ohio, ICRU-IAEA Meeting, 18-20 Mar. 2006; Iwata, Y. et al., "Alternating-Phase-Focused IH-DTL for Heavy-Ion Medical Accelerators", Proceedings of EPAC 2006, Edinburgh, Scotland; and Leitner, C. M. et al., "Status of the Superconducting ECR Ion Source Venus", Proceedings of EPAC 2000, Vienna, Austria.

The doses applied depend on the desired effect and the particular feedstock. For example, high doses can break chemical bonds within feedstock components and low doses can increase chemical bonding (e.g., cross-linking) within feedstock components.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, treatment in the presence of oxygen or even treatment with oxygen ions can be performed. For example, when nitrogen-containing functional groups are desirable, treatment in the presence of nitrogen or even treatment with nitrogen ions can be performed.

B. Other Forms of Energy

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient.

Electromagnetic radiation is subclassified as gamma rays, x rays, ultraviolet rays, infrared rays, microwaves, or radiowaves, depending on the wavelength.

For example, gamma radiation can be employed to treat the materials. Gamma radiation has the advantage of a significant penetration depth into a variety of material in the sample. Sources of gamma rays include radioactive nuclei, such as isotopes of cobalt, calcium, technetium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Various other devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 B2, the complete disclosure of which is incorporated herein by reference.

C. Electron Bombardment

1. Electron Beams

The feedstock may be treated with electron bombardment to modify its structure and thereby reduce its recalcitrance. Such treatment may, for example, reduce the average molecular weight of the feedstock, change the crystalline structure of the feedstock, and/or increase the surface area and/or porosity of the feedstock.

Electron bombardment via an electron beam is generally preferred, because it provides very high throughput and because the use of a relatively low voltage/high power electron beam device eliminates the need for expensive concrete vault shielding, as such devices are "self-shielded" and provide a safe, efficient process. While the "self-shielded" devices do include shielding (e.g., metal plate shielding), they do not require the construction of a concrete vault, greatly reducing capital expenditure and often allowing an existing manufacturing facility to be used without expensive modification. Electron beam accelerators are available, for example, from IBA (Ion Beam Applications, Louvain-la-Neuve, Belgium), Titan Corporation (San Diego, Calif., USA), and NHV Corporation (Nippon High Voltage, Japan).

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, from about 0.7 to 1 MeV, or from about 1 to 3 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

In some implementations, it is desirable to cool the material during electron bombardment. For example, the material can be cooled while it is being conveyed, for example by a screw extruder or other conveying equipment.

To reduce the energy required by the recalcitrance-reducing process, it is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates generally require higher line speeds, to avoid thermal decomposition of the material. In one implementation, the accelerator is set for 3 MeV, 50 mAmp beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.5 Mrad, e.g., at least 5, 10, 20, 30 or at least 40 Mrad. In some embodiments, the treatment is performed until the material receives a dose of from about 0.5 Mrad to about 150 Mrad, about 1 Mrad to about 100 Mrad, about 2 Mrad to about 75 Mrad, 10 Mrad to about 50 Mrad, e.g., about 5 Mrad to about 50 Mrad, from about 20 Mrad to about 40 Mrad, about 10 Mrad to about 35 Mrad, or from about 25 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 8 Mrad/pass can, in some cases, cause thermal degradation of the feedstock material.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 9 to 11 Mrad/pass. As discussed above, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about five percent by weight retained water, measured at 25° C. and at fifty percent relative humidity.

Electron bombardment can be applied while the cellulosic and/or lignocellulosic material is exposed to air, oxygen-enriched air, or even oxygen itself, or blanketed by an inert gas such as nitrogen, argon, or helium. When maximum oxidation is desired, an oxidizing environment is utilized, such as air or oxygen and the distance from the beam source is optimized to maximize reactive gas formation, e.g., ozone and/or oxides of nitrogen.

In some embodiments, two or more electron sources are used, such as two or more ionizing sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons. It is generally preferred that the bed of biomass material has a relatively uniform thickness, as previously described, while being treated.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the biomass material depends on the electron energy used and the dose applied, while exposure time depends on the power and dose.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 5-100, 5-50, 5-40, 10-50, 10-75, 15-50, 20-35 Mrad.

In some embodiments, the treatment is performed at a dose rate of between 5.0 and 1500.0 kilorads/hour, e.g., between 10.0 and 750.0 kilorads/hour or between 50.0 and 350.0 kilorads/hours. In other embodiments the treatment is performed at a dose rate of between 10 and 10000 kilorads/hr, between 100 and 1000 kilorad/hr, or between 500 and 1000 kilorads/hr.

2. Electron Sources

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, accelerates them through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scans them magnetically in the x-y plane, where the electrons are initially accelerated in the z direction down the tube and extracted through a foil window. Scanning the electron beam is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of biomass materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially from Ion Beam Applications (Louvain-la-Neuve, Belgium), the Titan Corporation (San Diego, Calif., USA), and NHV Corporation (Nippon High Voltage, Japan). Typical electron energies can be 0.5 MeV, 1 MeV, 2 MeV, 4.5 MeV, 7.5 MeV, or 10 MeV. Typical electron beam irradiation device power can be 1 KW, 5 KW, 10 KW, 20 KW, 50 KW, 60 KW, 70 KW, 80 KW, 90 KW, 100 KW, 125 KW, 150 KW, 175 KW, 200 KW, 250 KW, 300 KW, 350 KW, 400 KW, 450 KW, 500 KW, 600 KW, 700 KW, 800 KW, 900 KW or even 1000 KW.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments describe herein because of the larger scan width and reduced possibility of local heating and failure of the windows.

3. Electron Guns—Windows

When treated with an electron gun, the biomass is irradiated as it passes under a window, which is generally a metallic foil (e.g., titanium, titanium alloy, aluminum and/or silicon). The window is impermeable to gases, yet electrons can pass with low resistance while being impermeable to gasses. The foil windows are preferably between about 10 and 100 microns thick (e.g., a window can be 10 microns thick, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 microns thick). Thin windows dissipate less energy as an electron beam passes through them (e.g., the resistive heating is less since Power=I$^2$R) which is advantageous with respect to irradiating the target material (e.g., biomass) with as much energy as possible. Thin windows are also less mechanically strong and more likely to fail which causes increased expense and more downtime for the equipment.

The foil window can be cooled by passing air or an inert gas over the window. When using an enclosure, it is generally preferred to mount the window to the enclosure and to cool the window from the side outside of the enclosed conveying system to avoid lofting up any particulates of the material being irradiated.

The system can include more than one window, e.g., a primary window and a secondary window. The two windows may form the enclosure to contain the purging gases and/or the cooling gases. The secondary window may serve a function as a "sacrificial" window, to protect the primary window. The electron beam apparatus includes a vacuum between the electron source and the primary window, and breakage of the primary window is likely to cause biomass material to be sucked up into the electron beam apparatus, resulting in damage, repair costs, and equipment downtime.

The window can be polymer, ceramic, coated ceramic, composite or coated composite. The secondary window can be, for instance, a continuous sheet/roll of polymer or coated polymer, which can be advanced continuously or at intervals to provide a clean or new section to serve as the secondary window.

The primary window and the secondary window can be made from the same material, or different materials. For instance, the primary window foil can be made from titanium, scandium, vanadium, chromium, nickel, zirconium, niobium, molybdenum, ruthenium, rhodium, palladium, hafnium, tantalum, tungsten, rhenium, platinum, iridium, or alloys or mixtures of any of these. The secondary single-type window foil can be made from titanium, scandium, vanadium, chromium, nickel, zirconium, niobium, molybdenum, ruthenium, rhodium, palladium, hafnium, tantalum, tungsten, rhenium, platinum, iridium, beryllium, aluminum, silicon, or alloys or mixtures of any of these. The primary and secondary windows can be of the same material, mixture of materials, or alloy, or different materials, mixtures of material or alloys. One or both of the windows can be laminates of the same of different materials, mixtures of materials, or alloys.

One of more of the windows can have a support structure across its face. The term "single-type window", as used herein, means a window with no support structure across its face. The term "double-type window", as used herein, means a window with a support structure across its face, where the support structure effectively divides the surface of the window into two parts. Such a double-type window is shown in U.S. Pat. No. 5,877,582 to Nishimura. Additional support structures can also be used.

The primary window foil and the secondary window foil can both be made from low Z element. Alternatively, the primary window foil can be made from a high Z element, and the secondary window foil can be made from a low Z element.

The embodiments described herein do not preclude the inclusion of additional windows, which may have a protective function, or may be included to modify the radiation exposure.

The windows can be concave, flat or convex. It is generally preferred that the window be slightly convex, in a direction away from the direction of the cooling fluid. This curvature improves the mechanical strength of the window and increases the permitted temperature levels as well as allowing a better flow path for the cooling fluid. On the side of the scanning horn the curvature tends to be towards the vacuum (e.g., away from the cooling fluid) due to the vacuum (e.g., about $10^{-5}$ to $10^{-10}$ torr, about $10^{-6}$ to $10^{-9}$ torr, about $10^{-7}$ to $10^{-8}$ torr).

The cooling of the window and/or concave shape of the window become especially important for high beam currents, for example at least about 100 mA electron gun currents (e.g., at least about 110 mA, at least about 120 mA, at least about 130 mA, at least about 140 mA, at least about 150 mA at least about 200 mA, at least about 500 mA, at least about 1000 mA) because resistive heating is approximately related to the square of the current as discussed above. The windows can be any shape but typically are approximately rectangular with a high aspect ratio of the width to the length (where the width direction is the same as the width of the conveying system perpendicular to the conveying direction, and the length is the same as the direction of conveying). The distance of the window to the conveyed material can be less than about 10 cm (e.g., less than about 5 cm) and more than about 0.1 cm (e.g., more than about 1cm, more than about 2 cm, more than about 3 cm, more than about 4 cm). It is also possible to use multiple windows (e.g., 3, 4, 5, 6 or more) with different and varied shapes and configured in different ways. For example, a primary or secondary foil window can include one, two or more windows in the same plane or layered and can include one or more support structures. For example support structures can be a bar or a grid in the same plane and contacting the windows.

In some embodiments, the window that is mounted on the enclosed conveying system is a secondary foil window of a two foil window extraction system for a scanning electron beam. In other embodiments, there is no enclosure for conveying the biomass material, e.g., the biomass is conveyed in air under the irradiation device.

A two-foil window extraction system for a scanning electron beam has two windows, a primary and a secondary window. Generally the primary window is closest to the electron source, and is concave towards the top of the scanning horn due to the vacuum on that side of the window. The secondary foil window tends to be flatter but is also concave in the same direction. This curvature helps provide structural support to the window and is mechanically stronger than a flat window. Alternatively the windows can be flat or curved in any direction. The window foils are typically at least about 10 microns thick to about 30 microns thick (e.g., about 15-40 microns, about 20-30 microns, about 5-30 microns, about 8-25 microns, about 10-20 microns, about 20-25 microns thick). The distance between the front surface of the primary window foil and back surface of the secondary window foil is preferably less than 30 cm, more preferably less than 20 cm, and most preferably less than 10 cm. Sidewalls, in combination with the primary and secondary windows, can define an interior space. Electrons travel through both windows to impinge on and penetrate the material (e.g., biomass) disposed beneath. A first inlet can be included on one sidewall can be arranged to allow a cooling fluid (e.g., a liquid or a gas) to impinge on the primary window foil. The cooling fluid can run along the window and then reverse direction on meeting the far (opposite) wall and flow back generally through the center of the interior space and then out through an exhaust port and/or outlet. A second inlet can be included on the sidewall and can be arranged to allow cooling fluid to impinge on the secondary window foil in a similar fashion. Optionally more inlets (e.g., 2, 3, 4, 5, 6 or more) can bring cooling fluid to the primary and secondary window surfaces and multiple outlets (e.g., 2, 3, 4, 5, 6 or more) can allow the cooling fluid to exit the interior space. In some embodiments, one or more side walls can even be a mesh, screen or grate with many openings through which cooling gas can flow while providing structural support to the windows.

Such window systems are described in U.S. Provisional App. No. 61/711,801, by Medoff et al., which was filed on Oct. 10, 2012, the entire contents of which are incorporated herein by reference. A variety of configurations for such a system will also be known to those of ordinary skill in the art.

4. Electron Guns—Window Spacing

Although a large spacing between the windows can be advantageous, for example, for the reasons described above, the large spacing poses some disadvantages. One disadvantage of a large spacing between windows is that the electron beams will pass through a larger volume of cooling gas which can cause energy losses. For example a 1 MeV beam loses about 0.2 MeV/M of energy, a 5 MeV beam loses about 0.23 MeV/M and a 10 MeV beam loses about 0.26 MeV/M.

Therefore with a 1 MeV beam of electrons passing through 1 cm of air, the beam loses only 0.2% of its energy, at 10 cm of air, the beam loses 2% of its energy, at 20 cm this is 4% of its energy, while at 50 cm the energy loss is 10%. Since the electrons also have to travel from the secondary foil window to the biomass through additional air, the gap between the windows must be carefully controlled. Preferably, energy losses are less than about 20% (e.g., less than 10%, less than 5% or even less than 1%). It is therefore advantageous to minimize the spacing between the windows to decrease energy losses. Optimal spacing (e.g., average spacing) between the windows (e.g., between the surface side of the electron window foil and the facing surface of the secondary window foil) for the benefit of cooling as described above and for the benefit of reducing energy loss are between about 2 and 20 cm (e.g., between about 3 and 20 cm, between about 4 and 20 cm, between about 5 and 20 cm, between about 6 and 20 cm, between about 7 and 20 cm, between about 8 and 20 cm, between about 3 and 15 cm, between about 4 and 15 cm, between about 5 and 15 cm, between about 6 and 15 cm, between about 7 and 15 cm, between about 8 and 15 cm between about 3 and 10 cm, between about 4 and 10 cm, between about 5 and 10 cm, between about 6 and 10 cm, between about 7 and 10 cm, between about 8 and 10 cm).

One of ordinary skill in the art will balance the advantages and disadvantages of window spacing to suit their needs.

In some embodiments support structures for the windows can be used across the windows, although these types of structures are less preferred because of energy losses that can occur to the electron beam as it strikes these kinds of structures.

A large spacing between the windows can be advantageous because it defines a larger volume between the windows and allows for rapid flowing of a large volume cooling of for very efficient cooling. The inlets and outlets are between 1 mm and 120 mm in diameter (e.g., about 2 mm, about 5 mm about 10 mm, about 20 mm, about 50 mm or even about 100 mm). The cooling gas flow can be at between about 500-2500 CFM (e.g., about 600 to 2500 CFM, about 700-2500 CFM, about 800 to 2500 CFM, about 1000 to 2500 CFM, about 600 to 2000 CFM, about 700-2000 CFM, about 800 to 2000 CFM, about 1000 to 2000 CFM, about 600 to 1500 CFM, about 700-1500 CFM, about 800 to 1500 CFM, about 1000 to 1500 CFM). In some embodiments, about 50% of the gas is exchanged per about 60 seconds or less (e.g., in about 50 sec or less, in about 30 sec or less, in about 10 sec or less, in about 1 sec or less).

5. Electron Guns—Cooling and Purging Gases

The cooling gas in the two foil window extraction system can be a purge gas or a mixture, for example air, or a pure gas. In one embodiment, the gas is an inert gas such as nitrogen, argon, helium and or carbon dioxide. It is preferred to use a gas rather than a liquid since energy losses to the electron beam are minimized. Mixtures of pure gas can also be used, either pre-mixed or mixed in line prior to impinging on the windows or in the space between the windows. The cooling gas can be cooled, for example, by using a heat exchange system (e.g., a chiller) and/or by using boil off from a condensed gas (e.g., liquid nitrogen, liquid helium).

When using an enclosure, the enclosed conveyor can also be purged with an inert gas so as to maintain an atmosphere at a reduced oxygen level. Keeping oxygen levels low avoids the formation of ozone which in some instances is undesirable due to its reactive and toxic nature. For example, the oxygen can be less than about 20% (e.g., less than about 10%, less than about 1%, less than about 0.1%, less than about 0.01%, or even less than about 0.001% oxygen). Purging can be done with an inert gas including, but not limited to, nitrogen, argon, helium or carbon dioxide. This can be supplied, for example, from a boil off of a liquid source (e.g., liquid nitrogen or helium), generated or separated from air in situ, or supplied from tanks. The inert gas can be recirculated and any residual oxygen can be removed using a catalyst, such as a copper catalyst bed. Alternatively, combinations of purging, recirculating and oxygen removal can be done to keep the oxygen levels low.

The enclosure can also be purged with a reactive gas that can react with the biomass. This can be done before, during or after the irradiation process. The reactive gas can be, but is not limited to, nitrous oxide, ammonia, oxygen, ozone, hydrocarbons, aromatic compounds, amides, peroxides, azides, halides, oxyhalides, phosphides, phosphines, arsines, sulfides, thiols, boranes and/or hydrides. The reactive gas can be activated in the enclosure, e.g., by irradiation (e.g., electron beam, UV irradiation, microwave irradiation, heating, IR radiation), so that it reacts with the biomass. The biomass itself can be activated, for example, by irradiation. Preferably the biomass is activated by the electron beam, to produce radicals which then react with the activated or unactivated reactive gas, e.g., by radical coupling or quenching.

Purging gases supplied to an enclosed conveyor can also be cooled, for example below about 25° C., below about 0° C., below about −40° C., below about −80° C., below about −120° C. For example, the gas can be boiled off from a compressed gas such as liquid nitrogen or sublimed from solid carbon dioxide. As an alternative example, the gas can be cooled by a chiller or part of or the entire conveyor can be cooled.

6. Electron Guns—Beam Stops

In some embodiments the systems and methods include a beam stop (e.g., a shutter). For example, the beam stop can be used to quickly stop or reduce the irradiation of material without powering down the electron beam device. Alternatively the beam stop can be used while powering up the electron beam, e.g., the beam stop can stop the electron beam until a beam current of a desired level is achieved. The beam stop can be placed between the primary foil window and secondary foil window. For example, the beam stop can be mounted so that it is movable, that is, so that it can be moved into and out of the beam path. Even partial coverage of the beam can be used, for example, to control the dose of irradiation. The beam stop can be mounted to the floor, to a conveyor for the biomass, to a wall, to the radiation device (e.g., at the scan horn), or to any structural support. Preferably the beam stop is fixed in relation to the scan horn so that the beam can be effectively controlled by the beam stop. The beam stop can incorporate a hinge, a rail, wheels, slots, or other means allowing for its operation in moving into and out of the beam. The beam stop can be made of any material that will stop at least 5% of the electrons, e.g., at least 10%, 20%, 30%, 40%, 50%, 60%, 70%, at least 80%, 85%, 90%, 91%, 92%, 93%, 94%, 95%, 96%, 97%, 98%, 99% or even about 100% of the electrons.

The beam stop can be made of a metal including, but not limited to, stainless steel, lead, iron, molybdenum, silver, gold, titanium, aluminum, tin, or alloys of these, or laminates (layered materials) made with such metals (e.g., metal-coated ceramic, metal-coated polymer, metal-coated composite, multilayered metal materials).

The beam stop can be cooled, for example, with a cooling fluid such as an aqueous solution or a gas. The beam stop can be partially or completely hollow, for example with cavities.

Interior spaces of the beam stop can be used for cooling fluids and gases. The beam stop can be of any shape, including flat, curved, round, oval, square, rectangular, beveled and wedged shapes.

The beam stop can have perforations so as to allow some electrons through, thus controlling (e.g., reducing) the levels of radiation across the whole area of the window, or in specific regions of the window. The beam stop can be a mesh formed, for example, from fibers or wires. Multiple beam stops can be used, together or independently, to control the irradiation. The beam stop can be remotely controlled, e.g., by radio signal or hard wired to a motor for moving the beam into or out of position.

D. Treatment of Biomass Material—Sonication, Pyrolysis, Oxidation, Steam Explosion If desired, one or more sonication, pyrolysis, oxidative, or steam explosion processes can be used in addition to or instead of other treatments to further reduce the recalcitrance of the biomass material. These processes can be applied before, during and or after another treatment or treatments. These processes are described in detail in U.S. Pat. No. 7,932,065 to Medoff, the full disclosure of which is incorporated herein by reference.

II. Biomass Materials

As used herein, the term "biomass materials" includes lignocellulosic, cellulosic, starchy, and microbial materials.

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, for ethanol production, no additional nutrients (other than a nitrogen source, e.g., urea or ammonia) are required during fermentation of corncobs or cellulosic or lignocellulosic materials containing significant amounts of corncobs. Other products may require addition of trace metals, vitamins, or buffering capacity, but these adjustment are well within the knowledge of those of ordinary skill in the art.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example paper products as described in U.S. application Ser. No. 13/396,365 ("Magazine Feedstocks" by Medoff et al., filed Feb. 14, 2012), the full disclosure of which is incorporated herein by reference.

Cellulosic materials can also include lignocellulosic materials which have been de-lignified.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

The biomass material can also include offal, and similar sources of material.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 the full disclosure of which is incorporated herein by reference.

Any of the methods described herein can be practiced with mixtures of any biomass materials described herein.

III. Biomass Material Preparation—Mechanical Treatments

The biomass can be in a dry form, for example with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomass larger than the perforations or screen are not irradiated. These larger materials can be re-processed, for example by comminuting, or they can simply be removed from processing. In another configuration material that is larger than the perforations is irradiated and the smaller material is removed by the screening process or recycled. In this kind of a configuration, the conveyor itself (for example a part of the conveyor) can be perforated or made with a mesh. For example, in one particular embodiment the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example a portion of the conveyor can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to the conveyor by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming caboxylated groups. In one embodiment the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the biomass material. These processes can be applied before, during and or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the biomass material, increase the surface area of the biomass material and/or decrease one or more dimensions of the biomass material.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. For example, a feedstock material can be conveyed through ionizing radiation using a conveyor as described herein and then mechanically treated. Chemical treatment can remove some or all of the lignin (for example chemical pulping) and can partially or completely hydrolyze the material. The methods also can be used with pre-hydrolyzed material. The methods also can be used with material that has not been pre hydrolyzed. The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for "opening up," "stressing," breaking or shattering the biomass materials, making the cellulose of the materials more susceptible to chain scission and/or disruption of crystalline structure during the physical treatment.

Methods of mechanically treating the biomass material include, for example, milling or grinding. Milling may be performed using, for example, a hammer mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., 1/4- to 1/2-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated biomass materials, are described in further detail in U.S. Pat. App. Pub. 2012/0100577 A1, filed Oct. 18, 2011, the full disclosure of which is hereby incorporated herein by reference.

IV. Use of Treated Biomass Material

Using the methods described herein, a starting biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

V. Intermediates and Products

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols and polyols (e.g., glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

Other intermediates and products, including food and pharmaceutical products, are described in U.S. Pat. App. Pub. 2010/0124583 A1, published May 20, 2010, to Medoff, the full disclosure of which is hereby incorporated by reference herein.

VI. Production of Enzymes by Microorganisms

Filamentous fungi, or bacteria that produce cellulase, typically require a carbon source and an inducer for production of cellulase.

Lignocellulosic materials comprise different combinations of cellulose, hemicellulose and lignin. Cellulose is a linear polymer of glucose forming a fairly stiff linear structure without significant coiling. Due to this structure and the disposition of hydroxyl groups that can hydrogen bond, cellulose contains crystalline and non-crystalline portions. The crystalline portions can also be of different types, noted as I(alpha) and I(beta) for example, depending on the location of hydrogen bonds between strands. The polymer lengths themselves can vary lending more variety to the form of the cellulose. Hemicellulose is any of several heteropolymers, such as xylan, glucuronoxylan, arabinoxylans, and xyloglucan. The primary sugar monomer present is xylose, although other monomers such as mannose, galactose, rhamnose, arabinose and glucose are present. Typically, hemicellulose forms branched structures with lower molecular weights than cellulose. Hemicellulose is therefore an amorphous material that is generally susceptible to enzymatic hydrolysis. Lignin is a complex high molecular weight heteropolymer generally. Although all lignins show variation in their composition, they have been described as an amorphous dendritic network polymer of phenyl propene units. The amounts of cellulose, hemicellulose and lignin in a specific biomaterial depend on the source of the biomaterial. For example, wood derived biomaterial can be about 38-49% cellulose, 7-26% hemicellulose and 23-34% lignin depending on the type. Grasses typically are 33-38% cellulose, 24-32% hemicellulose and 17-22% lignin. Clearly lignocellulosic biomass constitutes a large class of substrates.

The diversity of biomass materials may be further increased by pretreatment, for example, by changing the crystallinity and molecular weights of the polymers.

The cellulase producing organism when contacted with a biomass will tend to produce enzymes that release molecules advantageous to the organism's growth, such as glucose. This is done through the phenomenon of enzyme induction as described above. Since there are a variety of substrates in a particular biomaterial, there are a variety of cellulases, for example, the endoglucanase, exoglucanase and cellobiase discussed previously. By selecting a particular lignocellulosic material as the inducer the relative concentrations and/or activities of these enzymes can be modulated so that the resulting enzyme complex will work efficiently on the lignocellulosic material used as the inducer or a similar material. For example, a biomaterial with a higher portion of crystalline cellulose may induce a more effective or higher amount of endoglucanase than a biomaterial with little crystalline cellulose.

One of ordinary skill in the art can optimize the production of enzymes by microorganisms by adding yeast extract, corn steep, peptones, amino acids, ammonium salts, phosphate salts, potassium salts, magnesium salts, calcium salts, iron salts, manganese salts, zinc salts, cobalt salts, or other additives and/or nutrients and/or carbon sources. Various components can be added and removed during the processing to optimize the desired production of useful products.

Temperature, pH and other conditions optimal for growth of microorganisms and production of enzymes are generally known in the art.

VII. Saccharification

The treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification process can be partially or completely performed in a tank (e.g., a tank having a volume of at least 4,000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a TWEEN® 20 or TWEEN® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

VIII. Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum,* and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei,* and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

Many microorganisms that can be used to saccharify biomass material and produce sugars can also be used to ferment and convert those sugars to useful products.

IX. Sugars

In the processes described herein, for example after saccharification, sugars (e.g., glucose and xylose) can be isolated. For example sugars can be isolated by precipitation, crystallization, chromatography (e.g., simulated moving bed chromatography, high pressure chromatography), centrifugation, extraction, any other isolation method known in the art, and combinations thereof.

X. Hydrogenation and Other Chemical Transformations

The processes described herein can include hydrogenation. For example glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts known in the art) in combination with $H_2$ under high pressure (e.g., 10 to 12000 psi). Other types of chemical transformation of the products from the processes described herein can be used, for example production of organic sugar derived products such (e.g., furfural and furfural-derived products). Chemical transformations of sugar derived products are described in U.S. application Ser. No. 13/934,704 filed Jul. 3, 2013, the disclosure of which is incorporated herein by reference in its entirety.

XI. Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub.

2012/0052536, filed Jul. 15, 2011, the complete disclosure of which is incorporated herein by reference.

"Fermentation" includes the methods and products that are disclosed International App. No. PCT/US2012/071083 (which was filed Dec. 20, 2012, was published in English as WO 2013/096693), the contents of both of which are incorporated by reference herein in their entirety.

Mobile fermenters can be utilized, as described in International App. No. PCT/US2007/074028 (which was filed Jul. 20, 2007, was published in English as WO 2008/011598 and designated the United States), the contents of which is incorporated herein in its entirety. Similarly, the saccharification equipment can be mobile. Further, saccharification and/or fermentation may be performed in part or entirely during transit.

XII. Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. saccharobutylicum, C. Puniceum, C. beijernckii*, and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*.

For instance, *Clostridium* spp. can be used to produce ethanol, butanol, butyric acid, acetic acid, and acetone. *Lactobacillus* spp., can be used to produce lactice acid.

Many such microbial strains are publicly available, either commercially or through depositories such as the ATCC (American Type Culture Collection, Manassas, Va., USA), the NRRL (Agricultural Research Sevice Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Many microorganisms that can be used to saccharify biomass material and produce sugars can also be used to ferment and convert those sugars to useful products.

XIII. Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

EXAMPLES

Example 1. Effect of Exogenous Fructose on Saccharification

This example tests whether or not exogenous fructose inhibits saccharification enzymes.

Three 225 mL Erlenmeyer flasks were prepared, each with 10 g of treated corn cob biomass (mesh size between 15 and 40, and irradiated to 35 Mrad with an electron beam) 100 mL of water and 2.5 mL of Duet Accelerase™ (Danisco). To the first, second, and third flask were added, respectively: 0 g, 5 g and 10 g of fructose. The flasks were covered with aluminum foil and set in an incubator shaker at 50° C. and 200 rpm for four days. The amount of xylose and glucose was monitored by HPLC. The results of the saccharification are shown in the table below.

TABLE 1

Saccharification under varying levels of exogenous fructose.

| Sample | Glucose yield (g/L) | Xylose yield (g/L) | % Glucose |
| --- | --- | --- | --- |
| 0 g added fructose | 17.9 | 13.8 | 100.0 |
| 5 g added fructose | 16.7 | 12.3 | 93.5 |
| 10 g added fructose | 18.1 | 12.6 | 101.3 |

Unlike glucose (a known inhibitor of cellobiase), 5% or 10% added fructose does not inhibit the saccharification of corncob.

Example 2. Effect of Xylose Isomerase on Saccharification

Glucose is a known inhibitor of cellobiase. This example tests if the conversion of glucose to the isomer fructose by xylose isomerase can increase saccharification.

Four 225 mL Erlenmeyer flasks were prepared, each with 10 g of treated corn cob biomass and 100 mL of water. The biomass was treated as described in Example 1. To the first, second, and third flask was added 2.5 mL of Duet Accelerase™ (Danisco). To the second, third, and fourth flasks were added, respectively: 1 g, 0.1 g and 0.1 g of glucose isomerase (Sweetzyme™, Aldrich). The flasks were covered with aluminum foil and set in an incubator shaker at 50° C. and 200 rpm for four days. The amount of xylose and glucose was monitored by HPLC. The results of the saccharification are shown in the table below.

TABLE 2

Effectiveness of cellulase with added xylose isomerase.

| Sample | Glucose yield (g/L) | Xylose yield (g/L) | % Glucose | % Xylose |
|---|---|---|---|---|
| 2.5 mL Duet | 22.6 | 16.9 | 100.1 | 100.0 |
| 2.5 mL Duet + 1 g GI | 28.3 | 20.6 | 125.2 | 122.3 |
| 2.5 mL Duet + 0.1 g GI | 24.6 | 18.5 | 109.0 | 109.4 |
| 0.1 g GI | 1.6 | Not detected | 6.9 | Not detected |

The addition of glucose isomerase was observed to increase the effectiveness of the cellulase enzyme, with flask 2 producing about 25% more sugars than flask 1.

Example 3. Use of a Strong Acid to Cleave Cellobiose

This example tests the use of a strong acid to cleave cellobiose to glucose, to increase saccharification yield. The strong acid used was Amberlyst-15™, a polystyrene sulfonic acid. This is a strongly acidic sulfonic acid macroreticular polymeric resin that is based on crosslinked styrene divinylbenzene copolymers. Published studies indicate that Amberlyst-15 can cleave the dimer cellobiose to glucose.

Three 225 mL Erlenmeyer flasks were prepared, each with 10 g of treated corn cob biomass, 100 mL of water and 2.5 mL Duet Accelerase™. The biomass was treated as described in Example 1. In the second flask 1 g of glucose isomerase (Sweetzyme™, Aldrich) was added; and in the third 1 g of glucose isomerase and 0.1 g of polystyrene sulfonic acid (Amberlyst-15™, DOW) was added.

The flasks were covered with aluminum foil and set in an incubator shaker at 50° C. and 200 rpm for four days. The amount of xylose and glucose was monitored by HPLC. The results of the saccharification are shown in the table below.

TABLE 3

Effect of an Acid on Saccharification.

| Sample | Glucose yield (g/L) | Xylose yield (g/L) | % Glucose | % Xylose | % Amerlyst-15 improved with GI |
|---|---|---|---|---|---|
| Duet alone | 21.1 | 16.1 | 100 | 100 | NA |
| Duet + GI | 26.5 | 19.2 | 125 | 119 | NA |
| Duet + GI + Amberlyst | 27.9 | 20.5 | 131 | 127 | 14 |

The results show an improvement in the saccharification with the addition of glucose isomerase. The experiment also shows an improvement in the saccharification with the addition of polystyrene sulfonic acid.

Example 4. Removal of Cellobiase

This example examines saccharification where cellobiase has been removed, while the endo- and exo-cellulases have been retained.

Chromatofocusing was used to separate the enzymes. Duet Accelerase™ (Danisco) was injected onto a Mono P column using an AKTA system. The endo- and exo-cellulases bound to the column, while the cellobiase passed through and was removed. The exo- and endo-cellulases were then eluted from the column by shifting the pH to 4.0. The resulting fractions were combined and immediately applied to a saccharification reaction.

TABLE 4

Accumulation of Cellobiose and Sugars in the Absence of Cellobiase.

| Sample | Cellobiose | Glucose | Xylose | Xylitol | Lactose |
|---|---|---|---|---|---|
| AKTA purified Duet | 1.057 | 4.361 | 5.826 | 0.556 | |
| Duet | 0.398 | 16.999 | 14.830 | 0.726 | |
| Corncob (no enzymes) | | 0.673 | | 0.550 | |
| Spun/Filtered Duet | | 17.695 | 15.053 | 0.770 | 1.052 |

The expected result was that without cellobiase, there would be an accumulation of cellobiose. Although the yield was low, the table below shows that a detectable amount of cellobiose was indeed generated.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of producing glucose, xylose, and fructose, the method comprising:
   saccharifying recalcitrance-reduced lignocellulosic biomass with one or more cellulases and an acid on a support in the presence of xylose isomerase at between 30° C. and 65° C. to produce a mixture comprising glucose, fructose, and xylose,
   wherein the acid on the support is polystyrene sulfonic acid.

2. The method of claim 1, wherein the one or more cellulases is an endoglucanase, an exo-splitting glucanase, a cellobiase, or a combination thereof.

3. The method of claim 1, wherein the xylose isomerase is produced from *Pseudomonas hydrophila, Escherichia intermedia, Bacillus megaterium, Paracolobacterium aerogenoides*, or combination thereof.

4. The method of claim 1, wherein the temperature is in the range of 60 to 65 degrees C.

5. The method of claim 1, wherein the pH is 7 or below.

6. The method of claim 1, wherein said saccharifying to produce the mixture takes place under conditions of a pH in the range of 3 to 7.

7. The method of claim 1, wherein the saccharifying to produce the mixture takes place under conditions of a pH in the range of 7 to 9.

8. The method of claim 1, wherein the concentration of xylose isomerase is in the range of 0.1 to 500 U/g cellulose.

9. The method of claim 1, wherein the recalcitrance-reduced biomass has been pre-treated with a treatment method selected from the group consisting of: bombardment with electrons, sonication, oxidation, pyrolysis, steam explosion, chemical treatment, mechanical treatment, and freeze grinding.

10. The method of claim 1, wherein the lignocellulosic biomass is selected from the group consisting of: wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, industrial waste, arracacha, buckwheat, banana, barley, cassava, kudzu, ocra, sago, sorghum, potato, sweet potato, taro, yams, beans, favas, lentils, peas, and mixtures of any of these.

11. The method of claim 1, further comprising inoculating the glucose, xylose, and fructose with an organism that metabolizes the glucose, but not the xylose, to form a metabolic product.

12. The method of claim 11, wherein the metabolic product is ethanol, butanol, butyric acid, acetic acid, acetone, or a combination thereof.

13. The method of claim 1, wherein the acid on the support is a sulfonic acid macroreticular polymeric resin that is based on crosslinked styrene divinylbenzene copolymers.

14. The method of claim 1, wherein the saccharification temperature is 40-50 degrees C.

15. The method of claim 1, wherein the saccharification temperature is greater than or equal to 40 degrees C. and less than or equal to 60 degrees C.

16. The method of claim 1, wherein the saccharification temperature is greater than or equal to 50 degrees C. and less than or equal to 60 degrees C.

* * * * *